(12) United States Patent
Matsumoto et al.

(10) Patent No.: US 6,260,994 B1
(45) Date of Patent: Jul. 17, 2001

(54) BATTERY-POWERED LIGHT SOURCE ARRANGEMENT FOR ENDOSCOPE

(75) Inventors: Seiji Matsumoto; Etsuo Nakano; Suwao Sato, all of Nagano (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 0 days.

(21) Appl. No.: 09/365,772

(22) Filed: Aug. 3, 1999

(30) Foreign Application Priority Data

Aug. 21, 1998 (JP) .................................................. 10-235456

(51) Int. Cl.[7] ........................................................ F21V 5/00
(52) U.S. Cl. ............................................ 362/574; 600/160
(58) Field of Search .................................. 362/551, 555, 362/558, 560, 573, 574; 385/117

(56) References Cited

U.S. PATENT DOCUMENTS 4,622,584 * 11/1986 Nagasaki ................................ 348/69
5,430,475 * 7/1994 Goto ....................................... 348/65
5,471,023 * 11/1995 Kaizu ..................................... 200/310
6,110,106 * 8/2000 MacKinnon ........................... 600/181

FOREIGN PATENT DOCUMENTS 63-33879 * 2/1988 (JP) .

* cited by examiner

Primary Examiner—Sandra O'Shea
Assistant Examiner—Hargobind S. Sawhney
(74) Attorney, Agent, or Firm—Young & Thompson

(57) ABSTRACT

A light source arrangement for a battery-powered light source unit of an endoscope comprises a cylindrical housing, a base disposed at one end of the housing, a plurality of LEDs connected to a flexible circuit board supported on the base and a focusing lens. A light guide for directing light emanating from the LEDs. The light guide comprises a reflective surface formed on an inner wall of the housing, a reflector having a concave reflective surface which is disposed at one end of the housing so as to surround the LEDs or a micro-lens array disposed in front of the LEDs with each micro lens aligned with the LED.

17 Claims, 4 Drawing Sheets

FIG. 4B
FIG. 4A
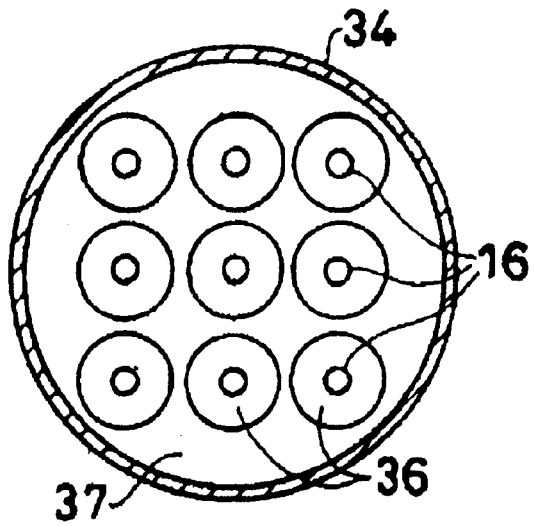
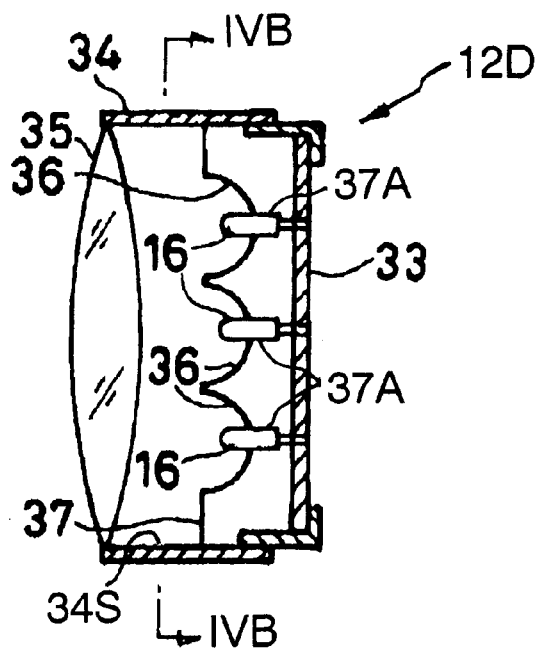
FIG. 4C
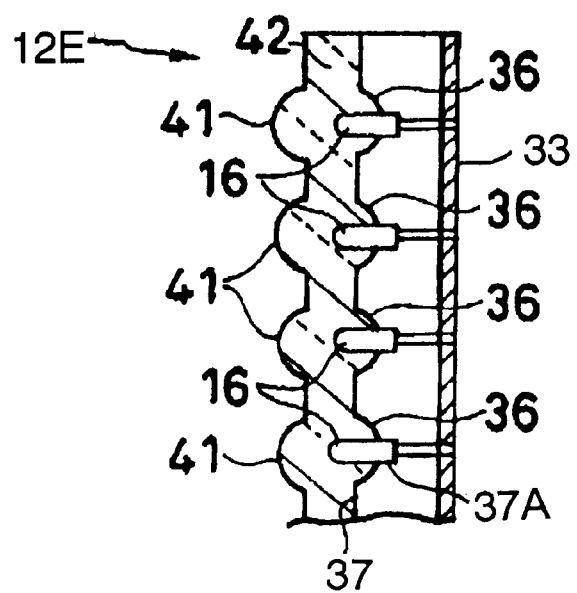

BATTERY-POWERED LIGHT SOURCE ARRANGEMENT FOR ENDOSCOPE

BACKGROUND OF THE INVENTION

1. Field of the Invention

This invention relates to a light source for an endoscope, and, in particular, to a light source arrangement for a battery-powered light source unit for an endoscope.

2. Description of Related Art

Typically, light source units are used to illuminate the inside of an organ of a human body while the inside of the organ is observed by, for example, an electronic endoscope. Such a light source unit is equipped with a lamp such as a halogen lamp and a xenon lamp as a light source. Light from the lamp is introduced into a light guide of the electronic endoscope to an illumination window and applied to a location to be observed and video displayed.

The light source, e.g. the halogen lamp and the xenon lamp, is energized by commercial power supply because it consumes electric power to somewhat significant extent. In view of less electric power consumption as well as miniaturization and lightening for portability, it is desired for the light source unit to use a battery-powered light source arrangement. In the field of electronic endoscope and information processing machines, miniaturization and electric power reduction of the battery-powered light source unit are advanced in regard to electronic circuits and, on the other hand, make very slow progress in regard to light source units due to utilization of a halogen lamp or a xenon lamp which ensures a somewhat great amount of light.

SUMMARY OF THE INVENTION

It is therefore an object of the invention to provide a light source arrangement for a battery-powered light source unit for an endoscope which realizes miniaturization and electric power reduction of the battery-powered light source unit.

The foregoing object of the invention is accomplished by providing a light source arrangement for a battery-powered light source unit of an endoscope which has an illumination system. The light source arrangement comprises a plurality of light emitting diodes arranged in, for example, a substantially ordinary matrix and supported on a base disposed at one end of a generally cylindrically-shaped housing, light guide means for guiding light emanating from the light emitting diodes forward, and a focusing lens disposed on another end of the generally cylindrically-shaped housing for focusing the light at a specified point of the illumination system of the endoscope.

According to a preferred embodiment of the invention, the light guide means comprises a reflective surface formed on an inner wall of the generally cylindrically-shaped housing. The light guide means may comprise a reflector formed with a concave reflective surface, such as a parabolic surface, disposed at the one end of the generally cylindrically shaped housing. In this case, the light emitting diodes are preferably placed approximately in a plane where one of focal points of the parabolic surface.

According to another preferred embodiment of the invention, the light guide means may comprise a reflector formed with the same number of concavities as the light emitting diodes and disposed at the one end of the generally cylindrically-shaped housing, each concavity having a reflective surface and being formed with a bore extending from its apex for receiving the light emitting diode therein. A micro-lens array having the same number of micro-lenses as the light emitting diodes may be further installed so as to cover the reflector formed with reflective cavities with each micro-lens aligned with the light emitting diode.

According to a further preferred embodiment of the invention, bare LEDs may be employed. In this arrangement, the light guide means comprises a micro-lens array integrally formed with the same number of micro-lenses as the bare light emitting diodes. The bare light emitting diode are arranged in, for example, an ordinary matrix between the base and the micro-lens array with each micro-lens aligned with the bare light emitting diode.

The light source arrangement of the invention in which the utilization is made of light emitting diodes which consume only small electric power and are energized by a battery can collects small amounts of light emanating from the respective light emitting diodes together by the light guide means so as thereby to provide a large amount of light and guide them to the focusing lens. The light source arrangement can enhance less electric power consumption and miniaturization and lightening for portability of the battery-powered light source unit.

BRIEF DESCRIPTION OF THE DRAWINGS

The above and other objects and features of the present invention will be understood from the following description of a specific embodiment thereof when considering in conjunction with the accompanying drawings, in which same or similar parts are denoted by the same reference numerals throughout the drawings, and where:

FIG. 4A is a cross-sectional view of a light source arrangement in accordance with another preferred embodiment of the invention;

FIG. 4B is a transverse section taken along line IVB—IVB of FIG. 4A;

FIG. 4C is a cross-sectional view of a variation of the light source arrangement shown in FIG. 4A;

DETAILED DESCRIPTION OF THE SPECIFIC EMBODIMENT

Figure 1:
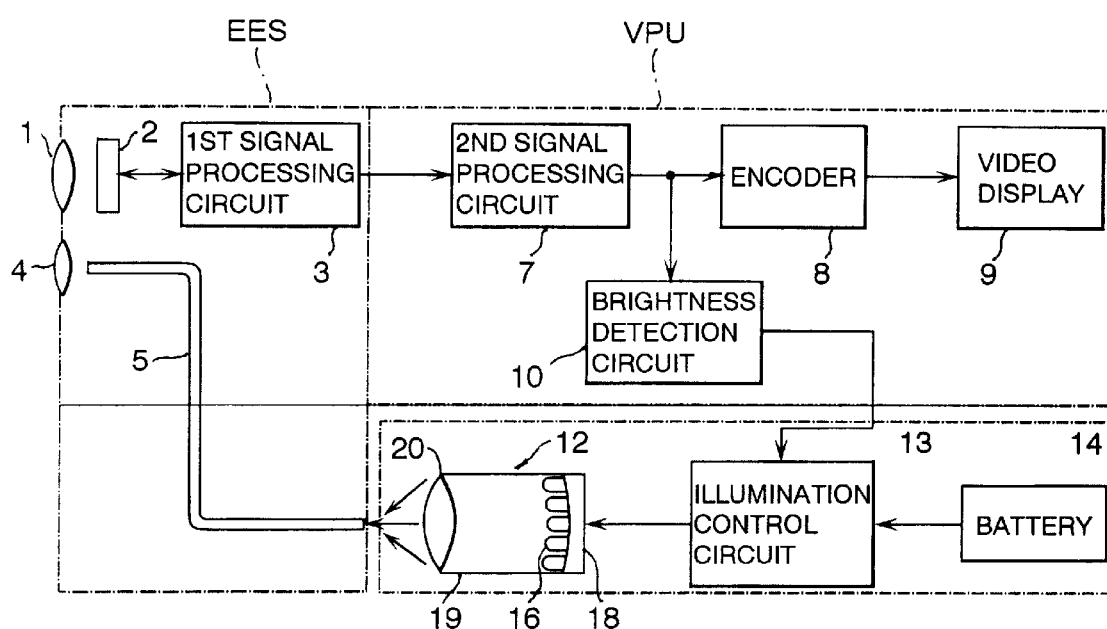
FIG. 1 is a schematic illustration of an electronic endoscope in which a battery-powered light source unit is provided with a light source arrangement of the invention.

Referring to the drawings in detail and, in particular, to FIG. 1 schematically showing an electronic endoscope system comprising an electronic endoscope EES, a video processing machine VPM and a battery-powered light source unit LSU of the invention, the electronic endoscope EES has a video producing system including an imaging lens 1, a solidstate imaging device such as a charge coupled device (CCD) 2 and a first signal processing circuit 3 and an illumination system including a light projection lens 4 and a light guide 5. Video signal provided by the CCD 2 upon which an optical image is projected by the objective 1 is sent to the first signal processing circuit 3 for signal amplification. The light projection lens 4 projects a beam of light which is introduced into the light guide 5 to illuminate an internal location of a human organ to be observed and/or video displayed through the light guide 5. The video processing machine VPM comprises a second signal processing circuit 7, an encoder 8, a brightness detection circuit 10 and a video display 9. The video signal amplified in the first signal processing circuit 3 is sent to the second signal processing circuit 7 and subjected to gamma processing and the like therein. The video isignal is finally sent to the video display 9 through the encoder 8. The brightness detection circuit 10 detects brightness of a video image based on the video signal from the second signal processing circuit 7. The battery-powered light source unit LSU comprises a light source arrangement 12, an illumination control circuit 13 and a battery 14. The light source arrangement 12 includes a plurality of light emitting diodes (LEDs) 16 supported on a base 18 and a focusing lens 20 which are installed in a cylindrical housing 19. The LED 16 emits light whose intensity is controlled according to brightness of an optical image by the illumination control circuit 13 and which is focused upon the incident end of the light guide 5 of the electronic endoscope EES by the focusing lens 20. The battery 14 mat be used to supply electric power to the light source arrangement 12 only or to the whole electronic endoscope system.

Figures 2A, 2B:
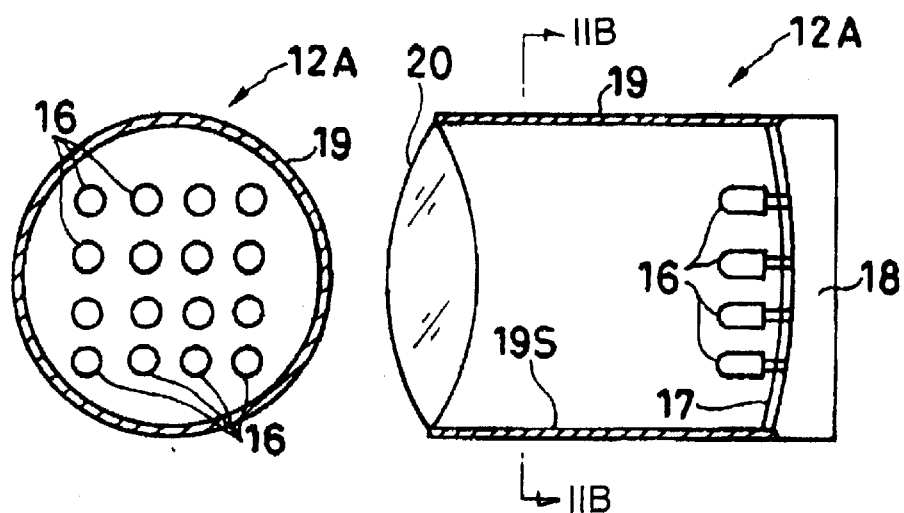
FIG. 2A is a cross-sectional view of a light source arrangement in accordance with a preferred embodiment of the invention.
FIG. 2B is a transverse section taken along line IIB—IIB of FIG. 2A.

FIGS. 2A and 2B show a light source arrangement 12A in accordance with a preferred embodiment of the invention. The light source arrangement 12A comprises a cylindrical housing 19, a circular base 18 forming a bottom of the cylindrical housing 19, an ordinary matrix of, for example, sixteen LEDs 16 which are connected to a flexible printed circuit board 17 which is placed on and attached to the base 18 having a spherical concave reflective surface and a focusing lens 20. A circuit on the flexible printed circuit board 17 has a wiring pattern for distributing energizing voltage input through a single pair of terminals to all of the sixteen LEDs 16. The cylindrical housing 19 is applied with a reflective coating layer 19S on its inside wall.

The LEDs 16 emit light when supplied with energizing voltage from the battery 14. The light is directed forward and focused on the incident end of the light guide 5 by the focusing lens 20. The focused light, which has a predetermined intensity at the incident end of the light guide 5 is transmitted by the light guide 5 and directed onto an internal location of a human organ by the light projection lens 4 as shown in FIG. 1. An optical image of the internal location is formed on the CCD 2 by the imaging lens 1. Video signal from the CCD 2 is processed by the first and second signal processing circuits 3 and 7 and transmitted to the video display 9 through the encoder 8 for display of the visual image on a screen. Simultaneously, the video signal is transmitted to the brightness detection circuit 10 which detects brightness of the optical image and generates a signal indicative of the optical image brightness. The illumination control circuit 13 controls the energizing voltage supplied to the respective LEDs 16 according to the brightness signal to vary the intensity of light from LED 16. Specifically, for example, the illumination control circuit 13 boosts the energizing voltage when the optical image has a brightness lower than a specified level or drops it when having a brightness higher than the specified level. The illumination control circuit 13 may be designed and adapted such that it variably controls the duration time of energization of the respective LEDs 16 so as thereby to change a charge storage time for which the CCD 2 is permitted to store charges.

According to the battery-powered light source unit LSU thus constructed, the utilization is made of LEDs 16, which consume only small electric power and are energized by a battery 14, in the light source arrangement 12A with the result of enhancing less electric power consumption and miniaturization and lightening for portability of the battery powered light source unit LSU.

Figure 3A:
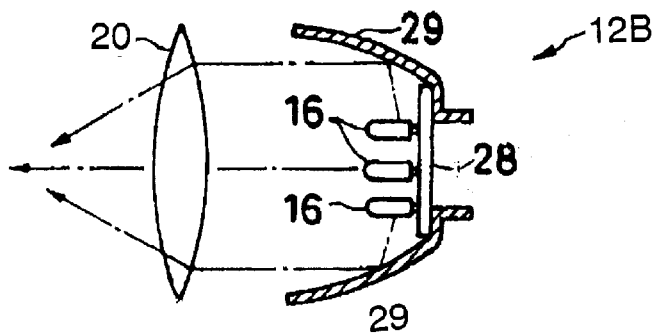
FIG. 3A is a cross-sectional view of a light source arrangement in accordance with another preferred embodiment of the invention.

FIG. 3A shows a light source arrangement 12B in accordance with another preferred embodiment of the invention. The light source arrangement 12B comprises a circular base 28, an ordinary matrix of, for example, sixteen LEDs 16 which are connected to a printed circuit board 28, an open-bottomed parabolic reflector 29 surrounding the matrix of LEDs 16, and a focusing lens 20. The same circuit as one of the flexible printed circuit board 17 shown in FIG. 2A is printed on the circuit board 28. The parabolic reflector 29 is formed with a high reflective surface on its inside wall. The LEDs 16 are position approximately in a plane where the focal point of the parabolic surface of the parabolic reflector 29 lies so as to reflect light emanating from LEDs 16 substantially in parallel to an axis of the parabolic surface and direct them to the focusing lens 20.

Figure 3B:
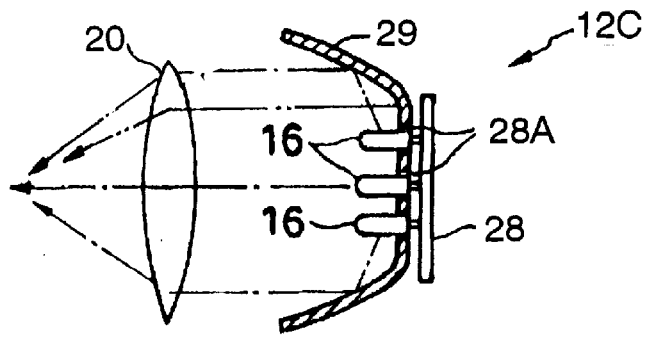
FIG. 3B is a cross-sectional view of a variation of the light source arrangement shown in FIG. 3A.

FIG. 3B shows a light source arrangement 12C, a variation of the light source arrangement 12B shown in FIG. 3A. The light source arrangement 12C comprises a circuit board 28, an ordinary matrix of, for example, sixteen LEDs 16 which are connected to a circuit printed on the circuit board 28, a parabolic reflector 29 having a flat bottom in which sixteen holes 31A are formed and is position approximately in a plane where the focal point of the parabolic surface of the parabolic reflector 29 lies, and a focusing lens 20. The same circuit as one of the flexible printed circuit board 17 shown in FIG. 2A is printed on the circuit board 28. The parabolic reflector 31 including the flat bottom is formed with a high reflective surface on its inside wall. The LEDs 16 are situated in the holes 28A, respectively. Light emanating from the LEDs 16 are reflected by the entire surface of the parabolic reflector 29 including the flat bottom and directed substantially in parallel to an axis of the parabolic surface to the focusing lens 20.

According to the battery-powered light source unit LSU thus constructed, the utilization is made of the parabolic reflector 29 in combination with LEDs 16, which consume only small electric power and are energized by a battery 14, in the light source arrangement 12B or 12C with the result of providing an increased amount of reflected light to be directed to the focusing lens 20 together with enhancing less electric power consumption and miniaturization and lightening for portability of the battery-powered light source unit LSU.

FIGS. 4A and 4B show a light source arrangement 12D in accordance with another preferred embodiment of the invention. The light source arrangement 12D comprises a cylindrical housing 34, a circular base 33 forming a bottom of the cylindrical housing 19, an ordinary matrix of, for example, nine LEDs 16 which are connected to the printed circuit, a reflector 37 and a focusing lens 20. The cylindrical housing 34 is applied with a reflective coating layer 34S on its inside wall. The same circuit as one of the flexible printed circuit board 17 shown in FIG. 2A is printed on the base 33. The reflector 37 is formed at the forward side thereof with nine hemispherical concavities 36 with reflective surfaces arranged in an ordinary matrix and bores 37A extending from apexes of hemispherical concavities 36, respectively. The LEDs 16 are situated in the bores 37A, respectively. Light emanating from the LEDs 16 are reflected by the reflective concavities 36 of the reflector 37 and directed to the focusing lens 20.

FIG. 4C shows a light source arrangement 12E, a variation of the light source arrangement 12D shown in FIGS. 4A and 4B. The light source arrangement 12E comprises a cylindrical housing (not shown), a circuit board 33 forming a bottom of the cylindrical housing, an ordinary matrix of, for example, sixteen LEDs 16 which are connected to a circuit printed on the circuit board 33, a micro-lens array 42, a reflector 37 and a focusing lens (not shown). The same circuit as one of the flexible printed circuit board 17 shown in FIG. 2A is printed on the circuit board 33. The reflector 37 is formed at the forward side thereof with sixteen hemispherical reflective concavities 36 arranged in an ordinary matrix and bores 37A extending from apexes of hemispherical reflective concavities 36, respectively. The LEDs 16 are situated in the bores 37A, respectively. The micro-lens array 42 is integrally formed with sixteen micro-lenses 41 arranged in the same ordinary matrix as the ordinary matrix of LEDs 16 and fills up the hemispherical reflective concavities 36. Light emanating from the LEDs 16 are reflected by the reflective concavity 36 of the reflector 37 and converged and directed to the focusing lens by the micro-lenses 41.

According to the battery-powered light source unit LSU thus constructed, the utilization is made of the reflector 37 formed with reflective concavities 36 or the combination of the reflector 37 formed with reflective concavities 36 and the micro-lens array 42 formed with micro-lenses 41 in the light source arrangement 12D or 12E with an effect of preventing diffusion of light emanating from LEDs 16 and directing the light to the focusing lens 35 with high efficiency.

Figure 5A:
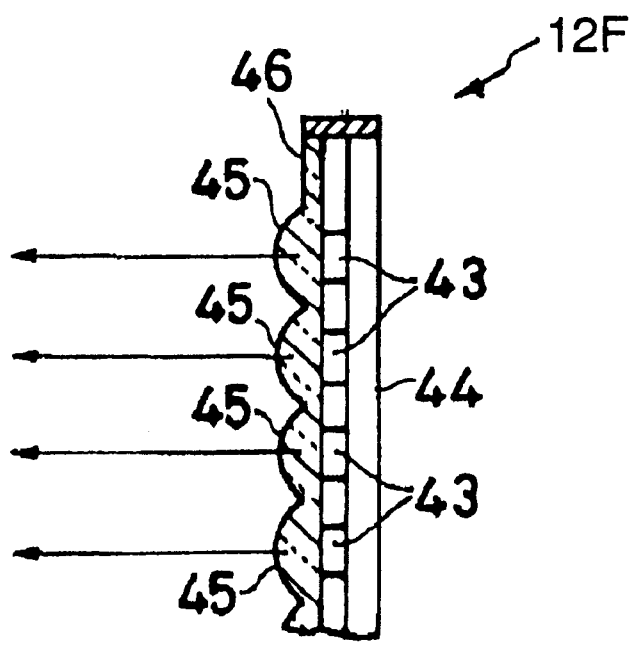
FIG. 5A is a cross-sectional view of a light source arrangement in accordance with still another preferred embodiment of the invention.

FIG. 5A shows a light source arrangement 12F in accordance with still another preferred embodiment of the invention. The light source arrangement 12F comprises a cylindrical housing (partly shown) 19, a circuit board 44 forming a bottom of the cylindrical housing, a number of, for example, sixteen bare LEDs 43 which are connected to a circuit printed on the circuit board 44, a micro-lens array 46 and a focusing lens (not shown). The micro-lens array 46 is integrally formed at the forward side thereof with sixteen micro-lenses 45 arranged in an ordinary matrix. The bare LEDs 43 are arranged in the same ordinary matrix of micro-lenses 46 and interposed between the circuit board 44 and the micro-lens array 46.

Figure 5B:
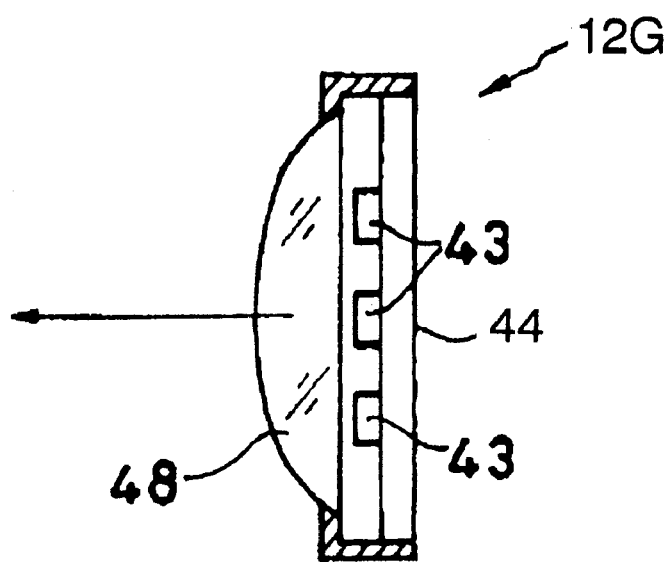
FIG. 5B is a cross-sectional view of a variation of the light source arrangement shown in FIG. 5A.

FIG. 5B shows a light source arrangement 12G, a variation of the light source arrangement 12F shown in FIG. 5A. The light source arrangement 12G includes a collimation lens 48 such as a Fresnel lens in place of the micro-lens array 46 of the light source arrangement 12F shown in FIG. 5A. A number of, for example, nine bare LEDs 43 are arranged in an ordinary matrix and connected to a circuit printed on a circuit board 44. The collimation lens 48 is positioned in front of the bare LED matrix to collimate light emanating from the bare LEDs 43 and direct them to a focusing lens (not shown).

According to the battery-powered light source unit LSU thus constructed, the utilization is made of the micro-lens array 46 or the collimation lens 48 in the light source arrangement 12F or 12G with an effect of gathering light emanating from bare LEDs 43 and directing the light to the focusing lens with high efficiency.

It is to be understood that although the present invention has been described with regard to preferred embodiments thereof, various other embodiments and variants may occur to those skilled in the art, which are within the scope and spirit of the invention, and such other embodiments and variants are intended to be covered by the following claims.

What is claimed is:

1. A light source arrangement of an endoscope which has an illumination system, comprising:
   a battery;
   a generally cylindrically-shaped housing with a reflective coating layer applied to an inner wall thereof;
   a plurality of light emitting diodes electrically connected to the battery;
   a base disposed at a proximal end of said generally cylindrically-shaped housing for supporting said light emitting diodes thereon;
   light guide means for guiding light emanating from said light emitting diodes forward; and
   a focusing lens disposed on a distal end of said generally cylindrically-shaped housing for focusing said light at a specified point of the illumination system of the endoscope.

2. A light source arrangement as defined in claim 1, wherein said light emitting diodes are arranged in a substantially ordinary matrix.

3. A light source arrangement as defined in claim 1, wherein said light guide means comprises a reflective surface formed on an inner wall of said generally cylindrically-shaped housing.

4. A light source arrangement as defined in claim 1, wherein said light guide means comprises a reflector formed with a concave reflective surface which is disposed at said one end of said generally cylindrically-shaped housing.

5. A light source arrangement as defined in claim 4, wherein said concave reflective surface comprises a parabolic surface and said light emitting diodes are arranged approximately in a plane where one of focal points of said parabolic surface.

6. A light source arrangement as defined in claim 1, wherein said light guide means comprises a reflector which is disposed at said proximal end of said generally cylindrically-shaped housing and integrally formed with the same number of concavities as said light emitting diodes, each said concavity having a reflective surface and being formed with a bore extending from said apex for receiving said light emitting diode therein.

7. A light source arrangement as defined in claim 6, wherein said reflective surface comprises a parabolic surface and each said light emitting diode is positioned in one of focal points of said parabolic surface.

8. A light source arrangement as defined in claim 6, and further comprising a micro-lens array having the same number of micro-lenses as said light emitting diodes, wherein said reflector is covered by said micro-lens array with each said micro lens aligned with said light emitting diode.

9. A light source arrangement as defined in claim 1, wherein said light guide means comprises a micro-lens array integrally formed with the same number of micro-lenses as said light emitting diodes, and said light emitting diode are of a bare type and arranged between said base and said micro-lens array with each said micro lens aligned with said light emitting diode.

10. A light source arrangement as defined in claim 9, wherein said light guide means comprises a collimation lens disposed at the proximal end of said generally cylindrically-shaped housing, and said light emitting diode are of a bare type and arranged between said base and said micro-lens array.

11. The light source arrangement of claim 1, wherein each of the plurality of light emitting diodes receives electrical power only from the battery.

12. An endoscope comprising:
   a battery;
   an objective lens;
   a charge coupled device receiving an image formed by the objective lens;
   a signal processing circuit connected to receive an output of the charge coupled device;
   an encoder receiving an output of the signal processing circuit;
   a video display receiving an output of the encoder;
   a light source arrangement comprising:
      a generally cylindrically-shaped housing with a reflective coating layer applied to an inner wall;
      a plurality of light emitting diodes electrically connected to the battery;
      a base disposed at one end of said generally cylindrically-shaped housing for supporting said light emitting diodes thereon;
      light guide means for guiding light emanating from said light emitting diodes forward; and
      a focusing lens disposed on another end of said generally cylindrically-shaped housing for focusing said light at a specified point of the illumination system of the endoscope;
   wherein the battery provides power to the entire endoscope.

13. A light source arrangement of an endoscope which has an illumination system, comprising:
   a battery;
   a generally cylindrically-shaped housing with a reflective coating layer applied to an inner wall;
   a plurality of light emitting diodes arranged in a matrix and electrically connected to the battery;
   a base disposed at one end of said generally cylindrically-shaped housing for supporting said light emitting diodes thereon;
   a parabolic reflector arranged to surround an entirety of the light emitting diode matrix so that each said light emitting diode lies generally in a plane of a focal point of the parabolic reflector;
   a focusing lens disposed on another end of said generally cylindrically-shaped housing for focusing said light at a specified point of the illumination system of the endoscope.

14. The light source arrangement of claim 13, wherein the base is disposed within the parabolic reflector.

15. The light source arrangement of claim 13, wherein the base is disposed so that the parabolic reflector lies between the light emitting diodes and the base.

16. The light source arrangement of claim 15, wherein the parabolic reflector comprises a separate aperture for each of the light emitting diodes.

17. The light source arrangement of claim 16, wherein each of the light emitting diodes is connected to the base through a respective one of the apertures.

* * * * *